United States Patent [19]
Saggar

[11] Patent Number: 5,702,455
[45] Date of Patent: Dec. 30, 1997

[54] EXPANDABLE PROSTHESIS FOR SPINAL FUSION

[76] Inventor: Rahul Saggar, 4 Bedford Ave., Brooklyn, N.Y. 11222

[21] Appl. No.: 684,770

[22] Filed: Jul. 3, 1996

[51] Int. Cl.$^6$ .................................................. A61F 2/44
[52] U.S. Cl. ............................................................ 623/17
[58] Field of Search ............................. 623/17; 606/61

[56] References Cited

U.S. PATENT DOCUMENTS

| | | | |
|---|---|---|---|
| 4,401,112 | 8/1983 | Rezaian | 128/92 |
| 4,553,273 | 11/1985 | Wu | 623/18 |
| 4,657,550 | 4/1987 | Daher | 623/17 |
| 4,834,757 | 5/1989 | Brantigan | 623/17 |
| 4,878,915 | 11/1989 | Brantigan | 623/17 |
| 4,936,848 | 6/1990 | Bagby | 623/17 |
| 5,015,247 | 5/1991 | Michelson | 606/61 |
| 5,059,193 | 10/1991 | Kuslich | 606/61 |
| 5,171,278 | 12/1992 | Pisharodi | 623/17 |
| 5,306,310 | 4/1994 | Siebels | 623/17 |
| 5,336,223 | 8/1994 | Rogers | 606/61 |
| 5,458,641 | 10/1995 | Ramirez | 623/17 |
| 5,534,029 | 7/1996 | Shima | 623/17 |

OTHER PUBLICATIONS

Information Sheet: "DePuy Motech Surgical Titanium Mesh" No. IOM595 0604-29-000 (Rev1) Published 1994.

Primary Examiner—John G. Weiss
Assistant Examiner—John M. Black
Attorney, Agent, or Firm—Robert W. J. Usher

[57] ABSTRACT

A spine stabilizing prosthesis has first and second hollow, cylindrical bearing members interconnected by a hollow, cylindrical jacking screw adjustable to expand the prosthesis within a cavity to bridge respective opposite axial ends of the bearing members into pressure engagement with opposing vertebral faces. Walls of the bearing members are perforated by a plurality of bone fragment admitting apertures and forming a bone fragment receptacle so that bone can grow and fuse completely through said bearing members when the prosthesis is installed in the cavity. Respective axial ends of the bearing members are formed with rings of vertebrae engaging teeth having ramp surfaces permitting sliding engagement when rotated in one direction and biting into the facing surfaces when rotated in the opposite direction resisting rotation to permit further expansion apart of the bearing members by rotation of the jacking screw.

4 Claims, 4 Drawing Sheets

EXPANDABLE PROSTHESIS FOR SPINAL FUSION

FIELD OF THE INVENTION

This invention relates to orthopaedic surgery and in particular to prosthesis for spinal fusion which permit bone to grow therethrough and thereby to share the body load.

BACKGROUND OF THE INVENTION

The standard surgical treatment for portions of the spine that are removed because of fracture or disease (e.g. corpectemy or diskectomy) involves bone fusion to span the cavity left by the removed vertebral portion. Whatever spans the cavity supports the load of the body above fully, or shares the load with some other means of fixation or prosthesis. It is desirable to obtain bone growth through the prosthetic because the more bone mass, the stronger the fusion. It is also desirable for the load to be shared by the grown bone, even ultimately to have the support taken by the bone rather than the prosthesis, because the prosthesis usually has a limited life. When inserting the prosthesis between the vertebra to be fused, it is necessary to have a tight fit in order to insure load sharing, while, according to Wolff's Law of Trabecular Architecture, bone grows in the direction of stress and, therefore, such tight fit also provides the requisite stress guiding the direction of bone growth.

A widely used prosthetic having the form of a one-piece tubular cage of titanium is manufactured by DePuy Motech Inc of Warsaw, Indiana and is described in their information sheet "The DePuy Motech Surgical Titanium Mesh" No. 10M595 0604-29-000 (Rev. 1), published in 1994.

However, although the tubular cage permits the requisite bone growth therethrough and provides a convenient receptacle in which to pack small bone fragments to promote osteogeneses, as a result of the cages fixed axial length, to obtain a tight fit, it is necessary to pull (force) the vertebrae apart and place the prosthetic therebetween. Such procedure increases the risk of injury being caused by vertebral movement in the highly sensitive area of the body, near the spinal chord.

It is also necessary to cut the cage to the appropriate length which can be an undesirably time consuming procedure for the doctor.

U.S. Pat. No. 5,458,641 issued in 1995 to Ramirez teaches a different approach which incorporates jackscrew or setscrew means formed as a turnbuckle by which the prosthesis can be adjusted in size but does not permit bone to grow across the cavity therethrough to eventually substitute for the support initially provided by the prosthesis. Furthermore, the design might eventually become unstable by over stressing the bone with screws.

U.S. Pat. No. 5,336,223 issued 1994 to Rogers also teaches an approach incorporating jackscrew means for expansion, but again which does not permit bone to grow through the prosthetic. It also requires time consuming preparation of the two vertebrae bordering the prosthetic to form cavities suitable for receiving the bearing elements thereof.

U.S. Pat. No. 5,306,310 issued 1994 to Siebels teaches helical springs adjustably interlinked for expansion. However, it can be relatively difficult to adjust by comparison with a simple jacking screw or turnbuckle-type mechanisms which may assure a tighter fit.

U.S. Pat. Nos. 4,657,550 issued 1987 to Daher and 4,553,273 issued 1985 to Wu teach approaches offer the ease of the jacking screw or turnbuckle mechanism but both require time consuming preparation of the vertebrae bordering the prosthetic and neither permit bone to grow through the prosthetic itself.

U. S. Pat. No. 4,401,112 issued in 1983 to Rezaian teaches an approach which also utilizes jackscrew means in the form of a turnbuckle but which does not permit bone to grow through the prosthetic itself depriving a relatively large area of bone growth.

SUMMARY OF THE INVENTION

Accordingly, it is an object of the invention to provide a prosthesis or spinal fixator which can be readily adjusted in situ to provide a pressure bridge between adjacent vertebrae, does not require extensive preparation of the vertebral surfaces and yet permits extensive bone growth therethrough.

According to one aspect of the invention there is provided, a spine stabilizing prosthesis for insertion between respective facing surfaces of respective vertebral portions above and below a cavity caused by removal of a portion of vertebra comprising:

first and second bearing members having respective remote, outer ends for bearing against said respective facing surfaces and, respective adjacent inner ends;

jacking screw adjustment means rotatively interconnecting respective adjacent inner ends of respective bearing portions for relative rotation to adjust separation of said bearing portions to bridge the cavity;

said bearing members having tubular, axially extending walls perforated by a plurality of bone fragment admitting apertures forming a bone fragment receptacle so that bone can grow and fuse through said bearing members when the prosthesis is installed in the cavity.

As the bone can grow and fuse throughout the bearing members, a suitably strong mass of fused bone can result to augment or eventually replace the support provided by the prosthesis.

Preferably, said jacking screw adjustment means comprises a single tubular shaft having a medial, tool engageable portion and opposite open ends formed with respective threads which are opposite, complementary opposite threads being formed on said first and said second bearing portions. This provides a structure which is hollow along the entire axis providing a bone receptacle extending completely across the cavity between the vertebral surfaces, enabling bone to fuse throughout the jacking screw providing a fused mass extending centrally between the facing surfaces of the vertebrae on opposite sides of the cavity.

Desirably, said respective remote, outer ends are formed with respective first and second rings of teeth for bearing against said respective facing surfaces, said teeth having ramp surfaces permitting sliding engagement with said facing surfaces when a respective bearing member is rotated in one rotational direction and biting into said facing surfaces when rotated in an opposite rotational direction.

Accordingly, with the prosthesis inserted in the cavity with bearing portions aligned with respective facing surfaces, at least one of the bearing portions can be rotated in a first sense relative to the shaft to increase the axial length of the prosthesis until spanning the cavity with the rings of teeth in sliding engagement with respective surfaces and the tool engageable portion then rotated in an opposite sense to urge the bearing portions further apart with the teeth preventing rotation to enable such expansion and being driven into anchoring engagement with the respective surfaces. This procedure significantly improves ease of installation.

According to another aspect of the invention, there is provided, a spine stabilizing prosthetic device for insertion between respective facing surfaces of respective vertebral portions above and below a cavity caused by removal of a portion of vertebra comprising:

first and second bearing portions having respective remote, outer ends and respective adjacent inner ends;

said respective remote, outer ends being formed with respective first and second rings of teeth for bearing against said respective facing surfaces;

jacking screw adjustment means rotatively interconnecting respective adjacent inner ends of respective bearing portions so that said bearing portions and said jacking screw adjustment means can be rotated relatively about a ring axis to adjust separation of said bearing portions to bridge the cavity; and, said teeth having ramp surfaces/barbs permitting sliding engagement with said facing surfaces in one rotational direction and biting into said surfaces in an opposite rotational direction.

BRIEF DESCRIPTION OF THE DRAWINGS

A specific embodiment of the invention will now be described with reference to the accompanying drawings in which.

DESCRIPTION OF PARTICULAR EMBODIMENT

Figure 1:
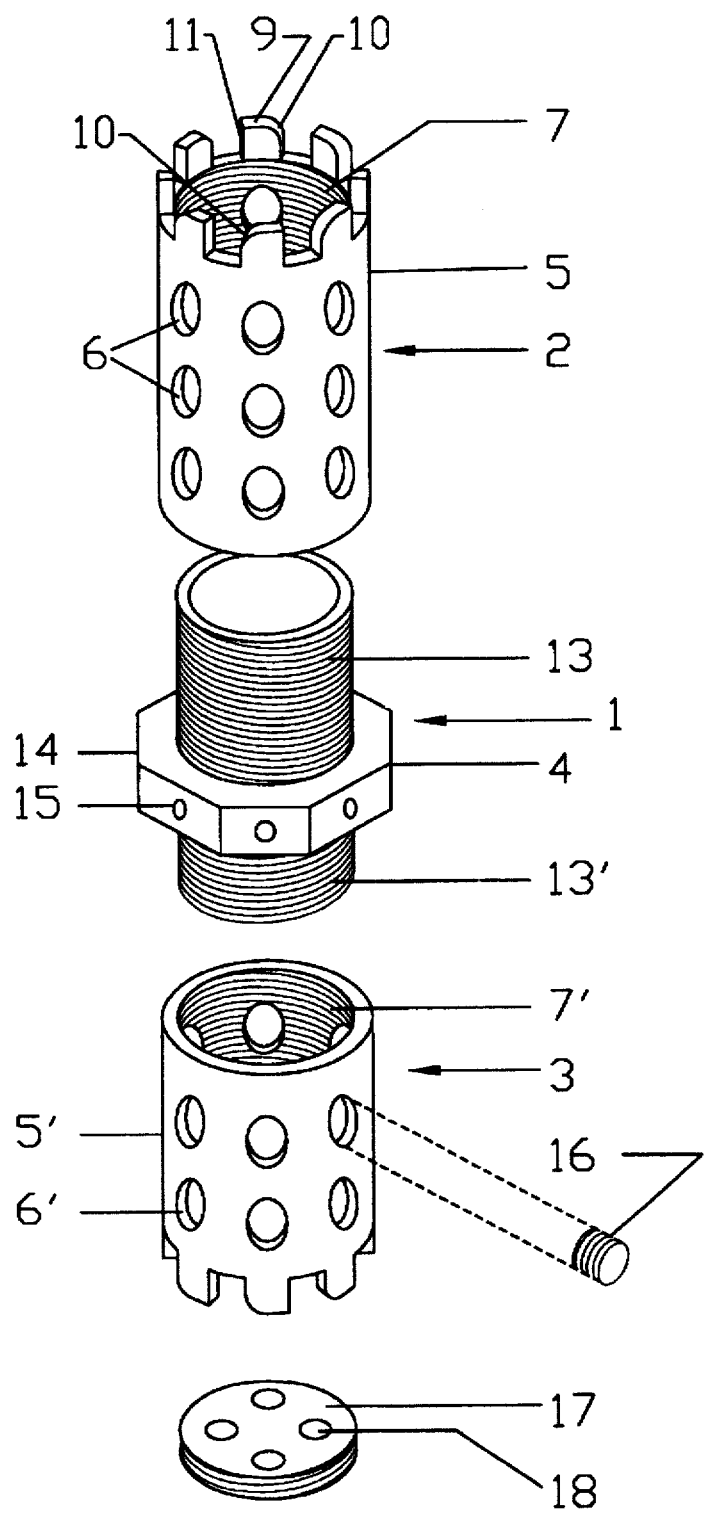
FIG. 1 is an exploded perspective view of a prosthesis according to the invention.
Figure 2:
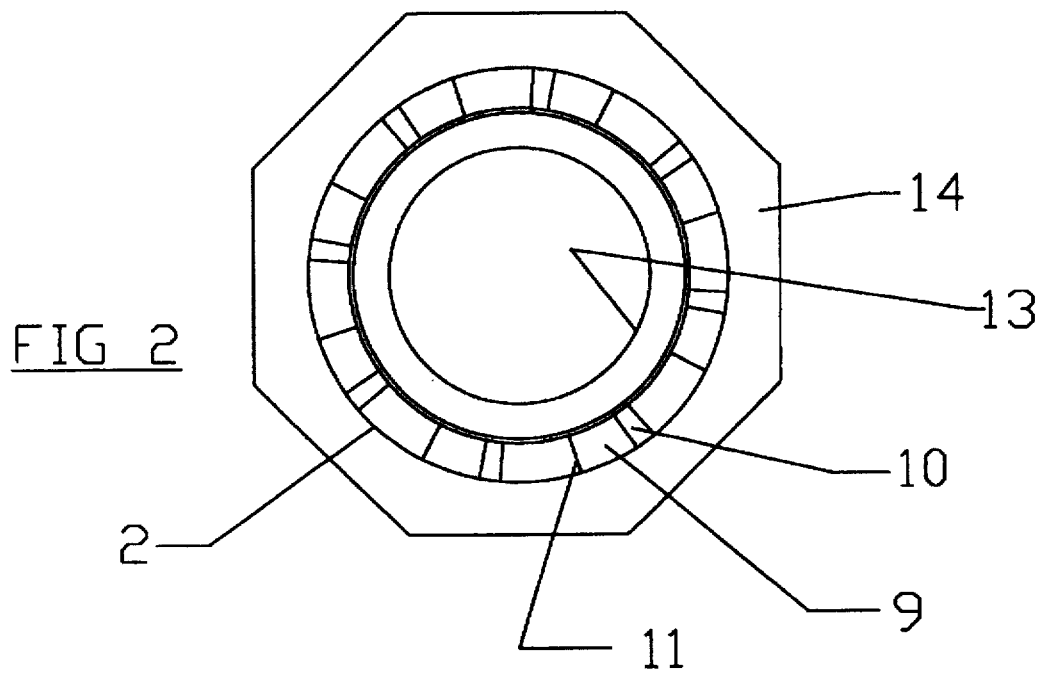
FIG. 2 is a plan view of the prosthesis of FIG. 1.
Figure 3:
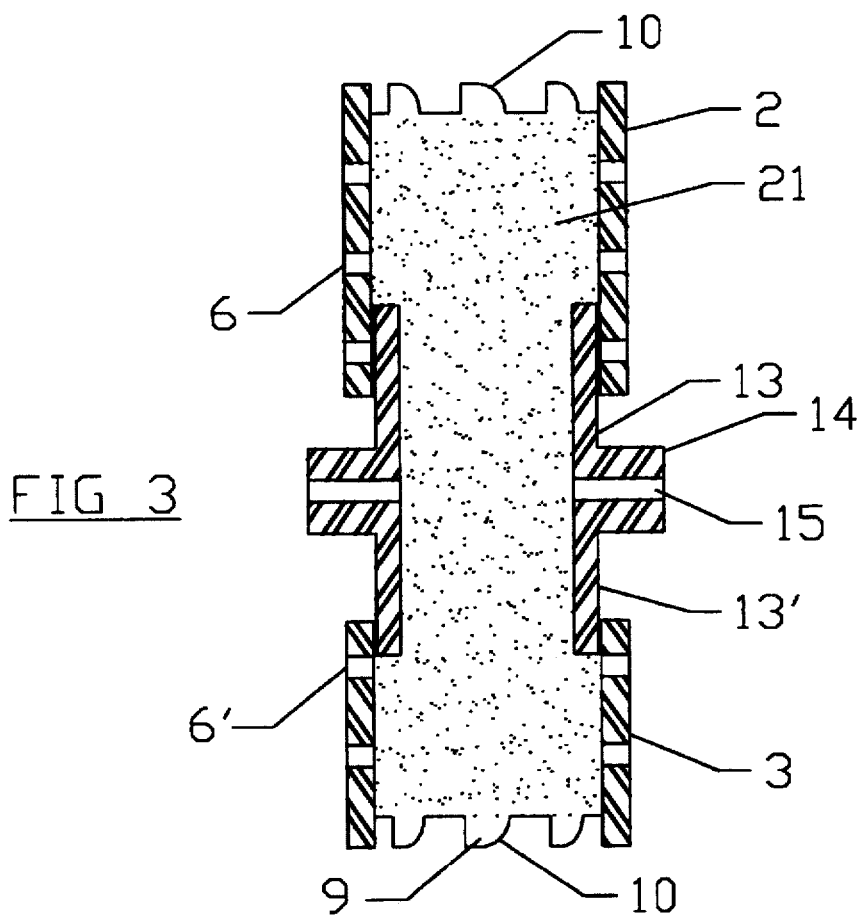
FIG. 3 is an axial cross-section of the prosthesis in an expanded condition, stuffed with bone paste.

The spinal fixator or prosthesis 1 comprises first and second bearing members 2 and 3, respectively, interconnected by a jacking screw adjustment member 4.

The bearing members 2 and 3 are of closely similar construction and formed as cylindrical tubes 5, 5' of drawn stainless steel (or, preferably, titanium) having walls perforated by bone fragment receiving apertures 6, 6' forming a cage-like bone fragment receptacle. Interior surfaces of the tubes have threads 7, 7' of opposite senses cut therein. Teeth or castellations 9 are formed on remote ends of the tubes and are ramp form presenting a smooth ramp or radiussed surface 10 in one circumferential or rotational direction and a sharp corner or barb 11 in the other.

The jacking screw adjustment member 4 comprises a single shaft having a medial, nut-form, tool engageable portion 14 and opposite ends formed with respective threads 13 and 13' which are opposite to each other and complementary to the threads 7 and 7', respectively, on the first and said second bearing portions. Adjustment tool and bone graft receiving apertures 15 are provided in each facet of the tool engageable portion 14.

Figure 4:
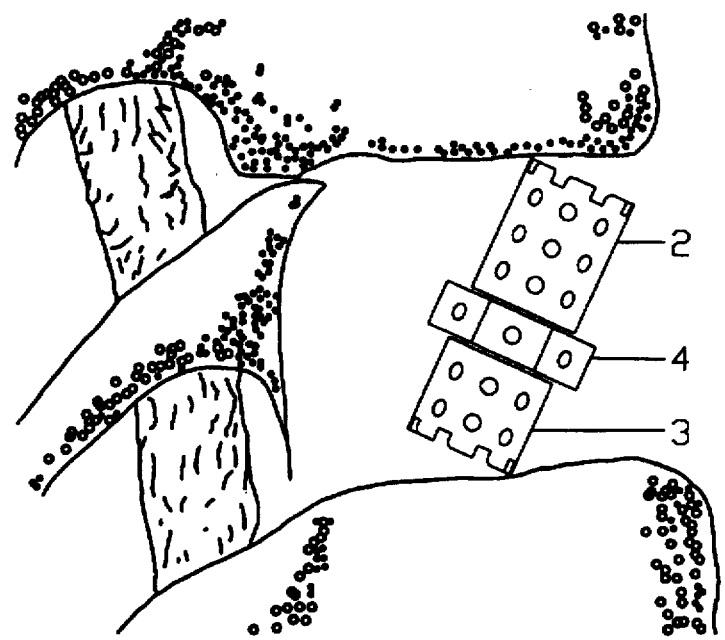
FIG. 4 is an elevational view showing an initial stage of insertion of the prosthesis into a vertebral cavity.
Figure 5:
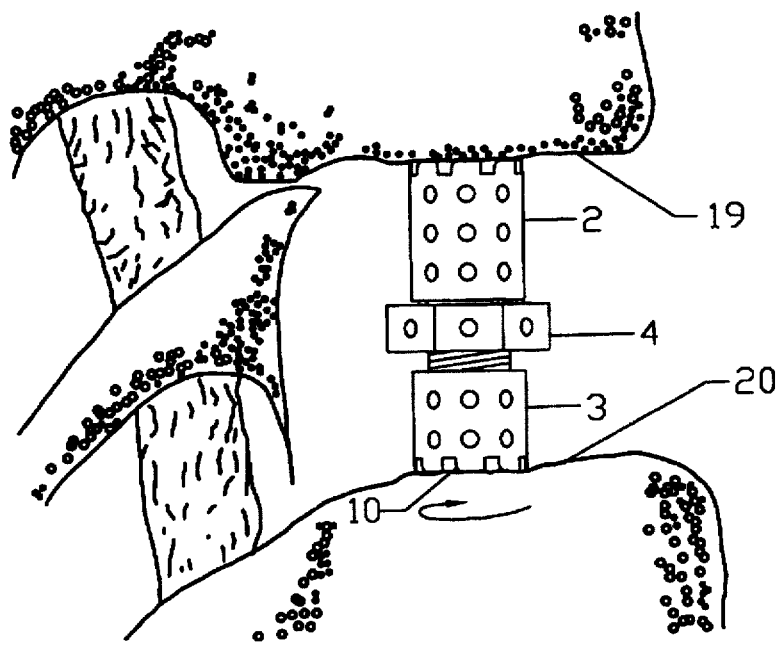
FIG. 5 is an elevational view showing the inserted prosthesis in an initial cavity spanning position.
Figure 6:
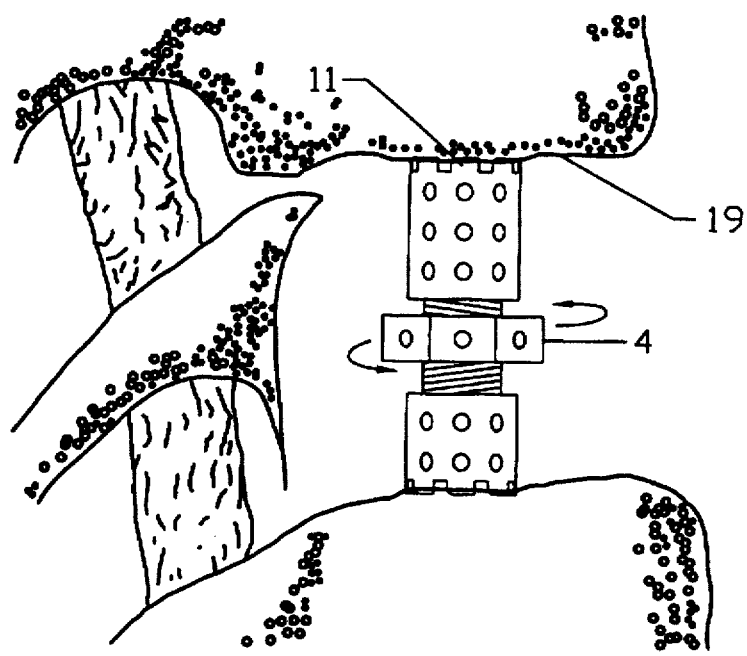
FIG. 6 is an elevational view showing the inserted prosthesis in a final anchoring position; and, FIG. 7 is an elevational view of the final assembly showing also a conventional staple.

In use, the prosthesis is stuffed with bone fragment paste 21 and inserted into the cavity via an incision in the posterior, with the bearing members retracted and in tilted condition for ease of entry, as shown in FIG. 4. Either the lower or upper members 3 or 2 is then rotated in a first sense relative to the shaft (by a user's fingers or by using a tommy bar), to increase the axial length of the prosthesis until spanning the cavity with the ramp surfaces leading, bringing the rings of teeth in sliding engagement with respective vertebral surfaces permitting rotation into a stable interference fit, as shown in FIG. 5. The tool engageable portion is then rotated in an opposite sense (using tommy bar or wrench) to urge both bearing members 2 and 3 further apart with the barbs leading, preventing rotation of either bearing member to permit further expansion and driving the teeth into penetrative, pressure applying, anchoring engagement with the respective vertebrae surfaces 19 and 20, as shown in FIG. 6. A set screw 16 is then inserted through one of the threaded apertures 3 into locking engagement with a threaded portion 13 or 13'.

Figure 7:
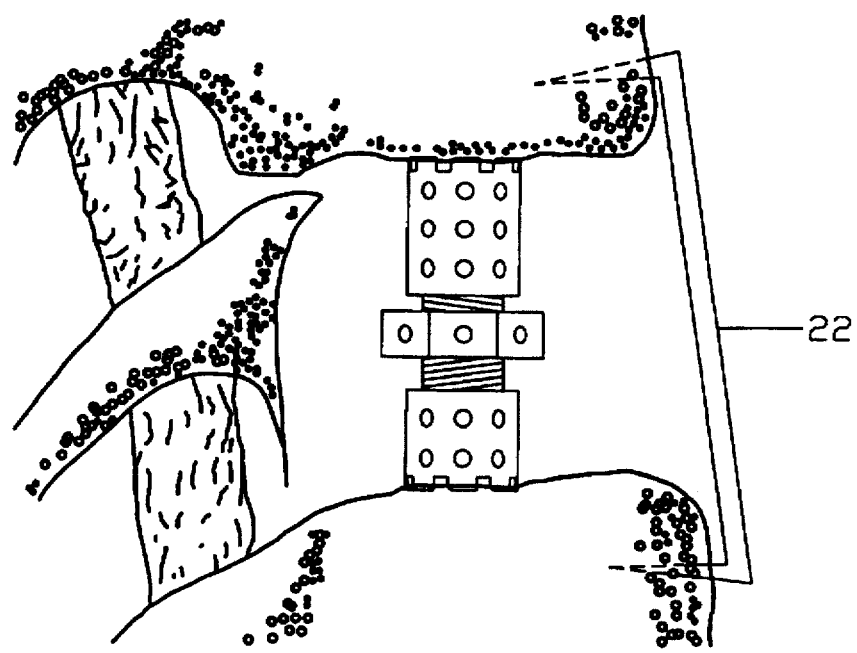

Conventional staples 22 (or rods, not shown) can be applied in conventional fashion for additional support, as shown in FIG. 7 and additional bone fragments 21 can be stuffed through the apertures 6 to fill any voids created by the expansion of the prosthesis and packed in the cavity around the prosthesis.

The bone fragments will grow and fuse completely throughout the prosthesis fusing also with the vertebral surface bone which is maintained under appropriate growth stimulating pressure for growth across the cavity to form a substantially homogeneous boney mass augmenting or possibly eventually substantially completely replacing the support provided by the prosthesis.

If desired, auxiliary strengthening discs 17 having bone admitting perforations 18 may be screwed into respective ends of respective support members prior to insertion of the prosthesis into the body, enabling the support members to be made of thinner material.

The ramp surfaces of the teeth facilitate unscrewing of a support member for removal and readjustment if necessary.

I claim:

1. A spine stabilizing prosthesis for insertion between respective facing surfaces of respective vertebral portions above and below a cavity caused by removal of a portion of vertebra comprising:

first and second bearing members having respective remote, outer ends for bearing against said respective facing surfaces and respective adjacent inner ends;

jacking screw adjustment means rotatively interconnecting respective adjacent inner ends of respective bearing members for relative rotation to adjust separation of said bearing members to bridge the cavity;

said jacking screw adjustment means comprises a single tubular shaft having a medial, tool engageable portion and opposite open ends formed with respective threads which are opposite, complementary opposite threads being formed on said first and said second bearing portions; and, said bearing members having tubular, axially extending walls perforated by a plurality of bone fragment admitting apertures forming a bone fragment receptacle so that bone can grow and fuse through said bearing members and said tubular shaft when the prosthesis is installed in the cavity.

2. A prosthesis according to claim 1 wherein, said respective remote, outer ends are formed with respective first and second rings of teeth for bearing against said respective facing surfaces, said teeth having ramp surfaces permitting sliding engagement with said facing surfaces when a respective bearing member is rotated in one rotational direction and biting into said facing surfaces when rotated in an opposite rotational direction.

3. A spine stabilizing prosthesis for insertion between respective facing surfaces of respective vertebral portions above and below a cavity caused by removal of a portion of vertebra comprising:

first and second bearing portions having respective remote, outer ends and respective adjacent inner ends;

said respective remote, outer ends being formed with respective first and second rings of teeth for bearing against said respective facing surfaces;

jacking screw adjustment means rotatively interconnecting respective adjacent inner ends of respective bearing portions so that said bearing portions and said jacking screw adjustment means can be rotated relatively about a ring axis to adjust separation of said bearing portions to bridge the cavity;

said teeth having ramp surfaces permitting sliding engagement with said facing surfaces in one rotational direction and biting into said surfaces in an opposite rotational direction; and, said jacking screw adjustment means comprising a single shaft having a medial, tool engageable portion and opposite ends formed with respective threads which are opposite, complementary opposite threads being formed on said first and said second bearing portions, so that, with the prosthesis inserted in the cavity with bearing portions aligned with respective facing surfaces, at least one of the bearing portions can be rotated in a first sense relative to the shaft to increase the axial length of the prosthesis until spanning the cavity with the rings of teeth in sliding engagement with respective surfaces and the tool engageable portion then rotated in an opposite sense to urge the bearing portions further apart and thereby drive the teeth into anchoring engagement with the respective surfaces.

4. A prosthesis according to claim 3 wherein, said shaft is tubular.

* * * * *